US 10,434,024 B2

United States Patent
St. Louis et al.

(10) Patent No.: US 10,434,024 B2
(45) Date of Patent: Oct. 8, 2019

(54) MODULAR DENTAL TOOL AND DOCKING STATION

(71) Applicants: Kavo Dental Technologies, LLC, Charlotte, NC (US); Kaltenbach & Voigt GmbH, Biberach (DE)

(72) Inventors: Robert Thomas St. Louis, Charlotte, NC (US); Michael Carl Dunaway, Charlotte, NC (US); Frank Ulrich Emde, Memmingen (DE); Amod Ashok Kher, Chicago, IL (US); Tyler Ray Harper, Gastonia, NC (US); Nathan Lamb Shippee, West Lebanon, NH (US); Johannes Sauter, Mittelbuch (DE); Patrick Niederreuter, Unterroth (DE)

(73) Assignees: KAVO DENTAL TECHNOLOGIES, LLC, Charlotte, NC (US); KALTENBACH & VOIGT GMBH, Biberach (DE)

( * ) Notice: Subject to any disclaimer, the term of this patent is extended or adjusted under 35 U.S.C. 154(b) by 89 days.

(21) Appl. No.: 15/236,854

(22) Filed: Aug. 15, 2016

(65) Prior Publication Data
US 2018/0042802 A1   Feb. 15, 2018

(51) Int. Cl.
*A61G 15/16*      (2006.01)
*A61C 1/00*       (2006.01)
*A61C 13/15*      (2006.01)

(52) U.S. Cl.
CPC ............ *A61G 15/16* (2013.01); *A61C 1/0007* (2013.01); *A61C 1/0023* (2013.01);
(Continued)

(58) Field of Classification Search
CPC ............... A61C 1/0023; A61C 1/0053; A61C 15/048–047; A61C 2204/002;
(Continued)

(56) References Cited

U.S. PATENT DOCUMENTS

| | | | |
|---|---|---|---|
| 3,696,283 A | | 10/1972 | Ackley |
| 4,123,845 A | * | 11/1978 | Fattaleh ................. A46B 17/04 433/99 |

(Continued)

FOREIGN PATENT DOCUMENTS

| | | |
|---|---|---|
| DE | 19508481 A1 | 9/1996 |
| EP | 0300317 A1 | 1/1989 |

(Continued)

OTHER PUBLICATIONS

Invitation to Pay Additional Fees and, Where Applicable, Protest Fee and Communication Relating to the Results of the Partial International Search for Application No. PCT/US2017/046726 dated Nov. 17, 2017 (13 pages).

(Continued)

*Primary Examiner* — Wade Miles
*Assistant Examiner* — Shannel N Wright
(74) *Attorney, Agent, or Firm* — Michael Best & Friedrich LLP

(57) ABSTRACT

A modular dental system, methods for controlling a modular dental tool, a dental system, a control module, and a treatment unit. In one embodiment, the modular dental system includes a modular dental system including a control module and a battery module. The control module includes a first end, a second end, a control sub-system, and a charging sub-system. The control sub-system is configured to communicatively couple to an attachment, detect an attachment identifier associated with the attachment when the attachment is removably attached to the first end of the control (Continued)

module, and control the attachment based on the attachment identifier. The battery module is configured to removably attach to the second end of the control module.

24 Claims, 12 Drawing Sheets

(52) U.S. Cl.
CPC ...... *A61C 19/004* (2013.01); *A61C 2204/002* (2013.01); *A61G 2203/20* (2013.01); *A61G 2205/60* (2013.01)

(58) Field of Classification Search
CPC .. A61C 2204/005; A61G 15/14; A61G 15/16; A61G 15/18; A61G 2203/20; A61G 2205/60; G06K 7/10009–10475; A61B 17/1626
USPC ......................................................... 433/126
See application file for complete search history.

(56) References Cited

U.S. PATENT DOCUMENTS

| | | | |
|---|---|---|---|
| 4,180,812 A | 12/1979 | Kaltenbach et al. | |
| 4,355,977 A | 10/1982 | Ota et al. | |
| 4,619,614 A | 10/1986 | Baba et al. | |
| 4,672,292 A | 6/1987 | Hernandez | |
| 4,705,038 A | 11/1987 | Sjostrom et al. | |
| 4,739,242 A | 4/1988 | McCarty et al. | |
| 4,818,231 A | 4/1989 | Steiner et al. | |
| 4,900,252 A * | 2/1990 | Liefke | A61C 3/04 433/27 |
| 5,269,794 A | 12/1993 | Rexroth | |
| 5,280,229 A | 1/1994 | Faude et al. | |
| 5,400,267 A | 3/1995 | Denen et al. | |
| 5,471,129 A | 11/1995 | Mann | |
| 5,561,881 A | 10/1996 | Klinger et al. | |
| 5,734,253 A | 3/1998 | Brake et al. | |
| 5,742,149 A | 4/1998 | Simpson | |
| 5,902,105 A * | 5/1999 | Uejima | A61C 19/041 433/27 |
| 5,947,729 A * | 9/1999 | Bell | A61C 1/0015 433/27 |
| 5,963,014 A | 10/1999 | Chen | |
| 6,018,227 A | 1/2000 | Kumar et al. | |
| D427,970 S | 7/2000 | Sage | |
| 6,126,670 A | 10/2000 | Walker et al. | |
| 6,204,632 B1 | 3/2001 | Nierescher et al. | |
| 6,293,795 B1 | 9/2001 | Johnson | |
| 6,860,764 B2 | 3/2005 | Khoury | |
| 6,929,476 B2 | 8/2005 | Katsuda et al. | |
| 7,057,374 B2 | 6/2006 | Freas et al. | |
| 7,086,111 B2 | 8/2006 | Hilscher et al. | |
| 7,119,515 B2 | 10/2006 | Senn et al. | |
| 7,439,463 B2 | 10/2008 | Brenner et al. | |
| 7,758,342 B2 | 7/2010 | Lewallen et al. | |
| 7,893,926 B2 | 2/2011 | Nyholm | |
| 8,035,487 B2 | 10/2011 | Malackowski | |
| 8,052,662 B2 | 11/2011 | Zelickson et al. | |
| 8,188,707 B2 | 5/2012 | McBurney | |
| 8,303,304 B2 | 11/2012 | Brennan et al. | |
| 8,400,104 B2 | 3/2013 | Adamczyk et al. | |
| 8,500,769 B2 | 8/2013 | Deng | |
| 8,680,412 B2 | 3/2014 | Horvath et al. | |
| 8,725,096 B2 | 5/2014 | Lint et al. | |
| 8,777,616 B2 | 7/2014 | Chronister | |
| 8,923,768 B2 | 12/2014 | Ma et al. | |
| 8,936,465 B2 | 1/2015 | Helfenbein et al. | |
| 2002/0064756 A1 | 5/2002 | Pagnini et al. | |
| 2002/0129454 A1* | 9/2002 | Hilscher | A61C 17/221 15/22.1 |
| 2002/0188183 A1 | 12/2002 | Kusakabe et al. | |
| 2004/0209223 A1* | 10/2004 | Beier | A61B 17/1626 433/99 |
| 2005/0080403 A1 | 4/2005 | Takahashi | |
| 2005/0147940 A1 | 7/2005 | Mace | |
| 2005/0282102 A1* | 12/2005 | Kert | A61B 5/0088 433/29 |
| 2006/0121787 A1 | 6/2006 | Bhavnani | |
| 2007/0254261 A1* | 11/2007 | Rosenblood | A61C 1/0015 433/98 |
| 2007/0270221 A1* | 11/2007 | Park | A46B 15/0002 463/37 |
| 2008/0014550 A1 | 1/2008 | Jones et al. | |
| 2008/0161783 A1* | 7/2008 | Cao | A61B 18/22 606/10 |
| 2008/0254404 A1 | 10/2008 | Heraud | |
| 2008/0293008 A1* | 11/2008 | Regere | A61C 1/0015 433/119 |
| 2009/0024118 A1* | 1/2009 | Vercellotti | A61B 17/1688 606/32 |
| 2009/0225060 A1* | 9/2009 | Rizoiu | A61C 1/0015 345/176 |
| 2009/0226856 A1* | 9/2009 | Sauter | A61B 17/1626 433/141 |
| 2010/0109644 A1* | 5/2010 | Pruckner | A61C 1/0015 324/120 |
| 2010/0112514 A1* | 5/2010 | Chen | A61C 1/0053 433/114 |
| 2010/0254149 A1* | 10/2010 | Gill | A61C 19/004 362/373 |
| 2010/0281636 A1* | 11/2010 | Ortins | A46B 9/04 15/4 |
| 2011/0243673 A1 | 10/2011 | Svagr | |
| 2012/0064483 A1* | 3/2012 | Lint | A61C 1/0023 433/101 |
| 2012/0171657 A1 | 7/2012 | Ortins et al. | |
| 2013/0008677 A1 | 1/2013 | Huifu | |
| 2013/0052607 A1* | 2/2013 | Gersh | A61C 19/004 433/27 |
| 2013/0119928 A1 | 5/2013 | Partovi | |
| 2013/0203010 A1* | 8/2013 | Inglese | A61B 1/00011 433/29 |
| 2014/0132210 A1 | 5/2014 | Partovi | |
| 2014/0191568 A1 | 7/2014 | Partovi | |
| 2014/0266636 A1 | 9/2014 | Larsen et al. | |
| 2014/0306654 A1 | 10/2014 | Partovi | |
| 2014/0349248 A1 | 11/2014 | Pond et al. | |
| 2015/0024335 A1 | 1/2015 | Sabourin | |
| 2015/0073399 A1* | 3/2015 | Boitor | A61B 18/22 606/15 |
| 2015/0257636 A1* | 9/2015 | Kohler | A61B 1/247 433/29 |
| 2015/0268803 A1 | 9/2015 | Patton et al. | |
| 2015/0374454 A1 | 12/2015 | Beerstecher et al. | |

FOREIGN PATENT DOCUMENTS

| | | |
|---|---|---|
| EP | 1725206 | 8/2011 |
| WO | 02071970 A1 | 9/2002 |
| WO | 2011130199 A1 | 10/2011 |

OTHER PUBLICATIONS

International Search Report and Written Opinion for Application No. PCT/US2017/046726 dated Apr. 24, 2018 (21 pages).
International Preliminary Report on Patentability for Application No. PCT/US2017/046726 dated Feb. 28, 2019 (11 pages).

* cited by examiner

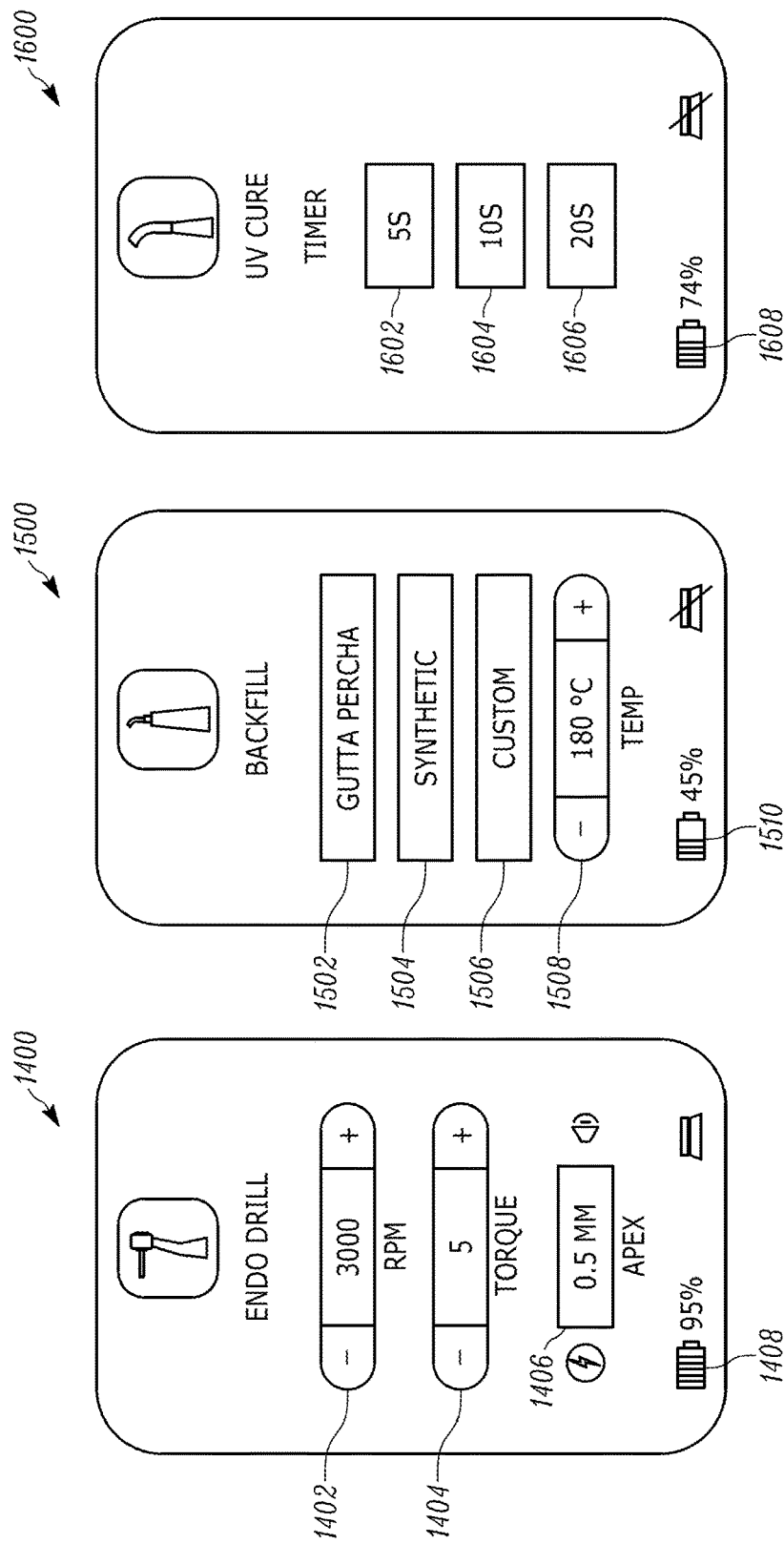

MODULAR DENTAL TOOL AND DOCKING STATION

FIELD

Embodiments relate to dental systems. More particularly, embodiments relate to modular dental tools and docking stations.

BACKGROUND

Many dental tools require a power cable, a conduit to carry for example water, air, or another media, a data cable, or a combination of such cables and conduits. These dental tools are typically designed for a particular purpose and cannot be used for different tasks or multiple purposes. A dentist or other dental professional performing a dental procedure or operation may need several single-purpose dental tools to complete that procedure. Each single-purpose dental tool may require one or more of a power cable, media conduit, or data cable to operate.

BRIEF DESCRIPTION OF THE DRAWINGS

Aspects of various embodiments will become apparent by consideration of the detailed description and accompanying drawings. The accompanying figures, where like reference numerals refer to identical or functionally similar elements throughout the separate views, together with the detailed description below, are incorporated in and form part of the specification, and serve to further illustrate embodiments, and explain various principles and advantages of those embodiments.

FIG. 15 is a diagram showing a graphical user interface for controlling an endodontic drill attachment in accordance with some embodiments.

FIG. 16 is a diagram showing a graphical user interface for controlling a backfill attachment in accordance with some embodiments.

FIG. 17 is a diagram showing a graphical user interface for controlling an ultraviolet (UV) curing light attachment in accordance with some embodiments.

Figure 1:
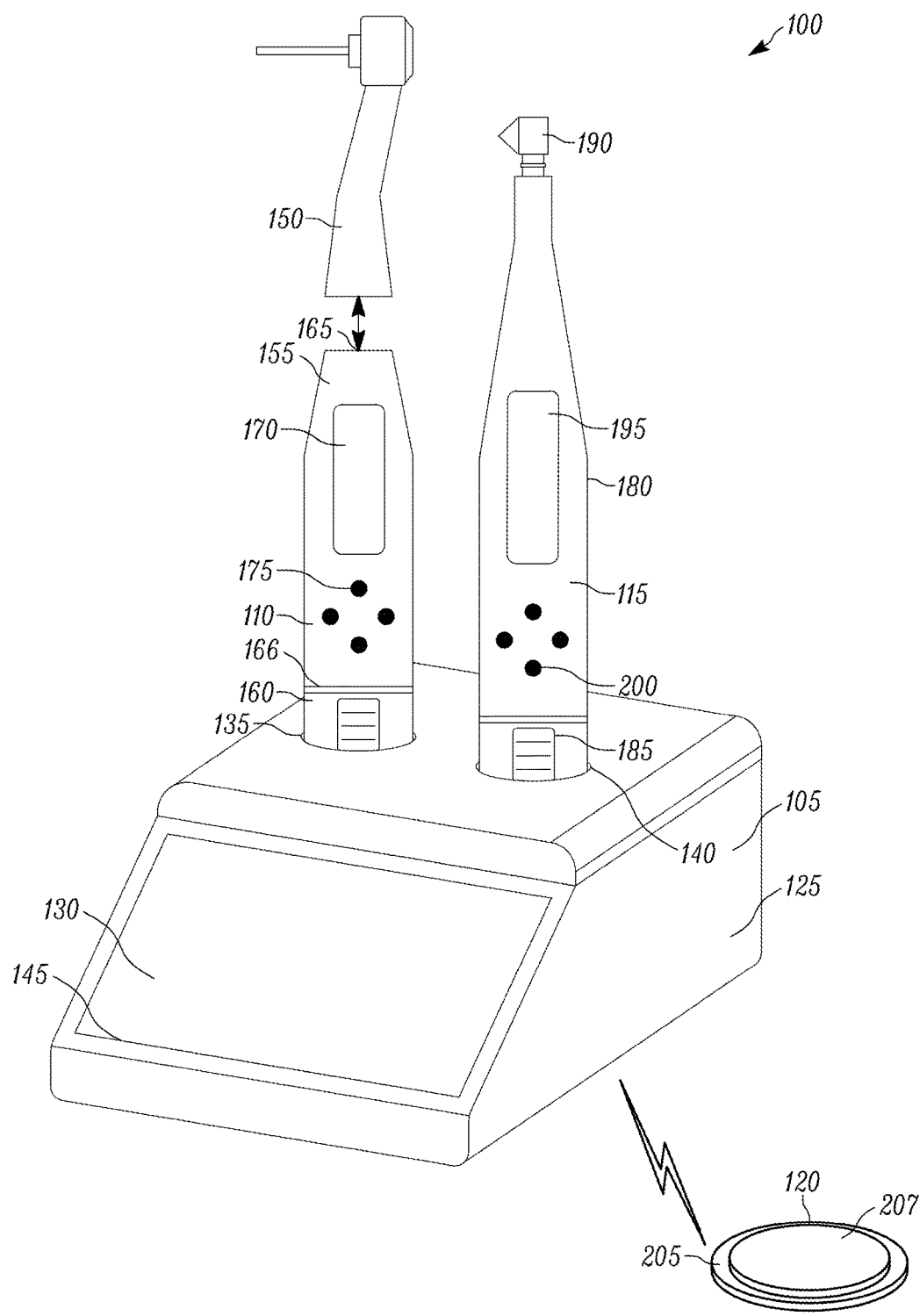
FIG. 1 is a diagram illustrating a dental system in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Managing multiple tools and various and numerous cables and conduits may be difficult. With a modular system, some of these cables and conduits may be eliminated.

One embodiment provides a modular dental system that includes a control module and a battery module. The control module includes a first end, a second end, a control sub-system, and a charging sub-system. The control sub-system is configured to communicatively couple to an attachment, detect an attachment identifier associated with the attachment when the attachment is removably attached to the first end of the control module, and control the attachment based on the attachment identifier. The battery module is configured to removably attach to the second end of the control module.

Another embodiment provides a method of controlling a modular dental tool. The method includes detecting, with a detector in a control module, a unique identifier when an attachment is removably attached to one end of the control module. The method includes receiving, with an electronic processor in the control module, the unique identifier. The method includes generating, with the electronic processor in the control module, a graphical user interface in response to receiving the unique identifier from the detector. The method includes operating the attachment using the graphical user interface.

Another embodiment provides a method of controlling a modular dental tool. The method includes detecting, with a detector in a docking station, a unique identifier when an attachment is removably attached to one end of a control module. The method includes receiving, with an electronic processor in the docking station, the unique identifier. The method includes generating, with the electronic processor in the docking station, a graphical user interface in response to receiving the unique identifier from the detector. The method includes operating the attachment using the graphical user interface.

Another embodiment provides a dental system. The dental system including a first modular dental tool. The first modular dental tool includes a first battery module, a first attachment, a second attachment, a second battery module, and a second control module. The first control module includes a first control sub-system and a first charging sub-system. The first battery module is configured to removably attach to the first charging sub-system at a first end of the first control module. The first attachment is configured to removably attach to a second end of the first control module opposite from the first end. The second attachment is configured to removably attach to the second end of the first control module in place of the first attachment. The second battery module is configured to removably attach to the first charging sub-system at the first end of the first control module in place of the first battery module. The second control module is configured to removably attach to the first battery module and the first attachment. The first attachment and the second attachment are different types of dental attachments.

Yet another embodiment provides a control module including a detector, a charging sub-system, and a control sub-system. The control sub-system is coupled to the detector, and the charging sub-system. The control module includes a first end configured to removably attach to a battery and a second end configured to removably attach to an attachment. The detector is configured to communicably couple to the attachment when the attachment is removably disposed on the control module. The detector is configured to detect a unique identifier associated with the attachment.

FIG. 1 is a diagram illustrating a dental system 100 (sometimes referred to as a "modular dental system"), in accordance with some embodiments. In the example of FIG. 1, the dental system 100 is a cordless or cable-less dental system that includes a docking station 105, and a modular dental tool 110. The dental system 100 also includes a single-purpose dental tool 115 and an input control. In certain embodiments, the input control is a wireless foot pedal 120 that is wirelessly connected to the docking station 105. However, in other embodiments the input control may be directly linked to the modular dental tool 110, the single-purpose dental tool 115, or both to provide control. In addition, other control devices, both wired and wireless and not only foot pedals, could be used in other embodiments. The dental system 100, including the docking station 105, may be part of a larger dental "treatment unit." A dental "treatment unit" may include a dental chair for a patient, an x-ray imaging system, a display that may be connected to both the x-ray imaging system and a patient records and management system, sources of water, electricity, and pressurized air, and plumbing fixtures, such as a spit sink. In one example, the docking station 105 is integrated with or into a treatment unit as is described below with respect to FIG. 2. For example, the docking station 105 may be sized, shaped, or otherwise configured to be supported by a shelf, shaft, or other support mechanism of a treatment unit.

The dental system 100 may be used to perform a variety of dental procedures. In one example, a user (for example, a dental technician, surgeon, or other suitable person) may use the modular dental tool 110 as an endodontic drill. The single-purpose dental tool 115 may be used for its designed purpose, for example, as an intra-oral camera. The two tools, modular dental tool 110 and single-purpose dental tool 115 may be used, for example, to perform an endodontic procedure.

In the example illustrated in FIG. 1, the docking station 105 includes a housing 125 and a display 130. The docking station 105 also includes a control sub-system and a charging sub-system as described in greater detail below. In some embodiments, docking station 105 is configured to electromagnetically couple and physically support a modular dental tool 110 and a single-purpose dental tool 115. In one example, as illustrated in FIG. 1, housing 125 includes two recesses 135 and 140 having a diameter or a width that is slightly larger than the diameter or the width of modular dental tool 110 and single-purpose dental tool 115, respectively.

Additionally, as illustrated in FIG. 1, housing 125 includes a display recess 145 that is slightly larger than the size of the display 130. In some embodiments, display 130 is a touch screen (for example, resistive or capacitive) or a similar device that also acts as an input device so that a user (for example, using a finger, a gloved finger, or a stylus) may interface with a control sub-system of the docking station 105 (described in greater detail below). In some embodiments, the display 130 is configured to be removable from the display recess 145 in the housing 125 that supports the display 130. The display 130 may include one or more electronic processors (which may be referred to herein collectively as a "display processor"). In some embodiments, the display of a dental treatment unit may be used in place of or in conjunction with the display 130.

The modular dental tool 110 includes an attachment 150, a control module 155, and a battery 160. The control module 155 includes a first end 165 and a second end 166. The attachment 150 is removably attached to the first end 165 and the battery 160 is removably attached to the second end 166 of the control module 155. The battery 160 is typically rechargeable. In the embodiment illustrated in FIG. 1, the attachment 150 is an endodontic drill. However, the attachment 150 may be a number of different dental tool heads that may removably attached to control module 155 (as will be described in greater detail below).

As illustrated in FIG. 1, the control module 155 includes a display 170 and a user input interface 175. The control module 155 also includes a control sub-system, a charging sub-system, and a motor as described in greater detail below.

In the embodiment illustrated in FIG. 1, the user input interface 175 is a directional pad with four buttons. However, in other embodiments, the user input interface 175 may include a variety of different physical or digital user interface arrangements. For example, the display 170 may be a touch screen display that includes a second user input interface with digital or "soft" buttons as part of a graphical user interface as will be described in greater detail below.

The single-purpose dental tool 115 includes a housing 180 and a battery 185. The battery 185 is also rechargeable. In some embodiments, the single-purpose dental tool 115 includes some of the components of the modular dental tool 110 as described above. In the embodiment illustrated in FIG. 1, the housing 180 supports a single-purpose dental tool head 190, a display 195, and a user input interface 200. In the example of FIG. 1, the single-purpose dental tool head 190 includes an intra-oral camera. In some embodiments, the battery 185 of the single-purpose dental tool 115 is interchangeable with the battery 160 of the modular dental tool 110. The single-purpose dental tool 115 also includes a control sub-system, a charging sub-system, and an electrical output device (as described in greater detail below).

The displays 130, 170, and 195 may include a liquid-crystal display (LCD), light-emitting diode display (LED), electroluminescent display (ELD), organic light-emitting diode display (OLED), or other suitable display. In the embodiment illustrated in FIG. 1, the user input interface 200 is a directional pad with four buttons. However, in other embodiments, the user input interface 200 may include a variety of different physical or electronic user interface arrangements. For example, the displays 130, 170, and 195 may be a touch screen display that includes a second user input interface with soft keys or soft buttons as part of a graphical user interface as will be described in greater detail below.

The wireless foot pedal 120 includes a housing 205 and one or more user input interfaces 207. The wireless foot pedal 120 also includes a control sub-system disposed within the housing 205 as will be described in greater detail below. The one or more user input interfaces 207 include one or more buttons, pressure sensitive switches, or other suitable user input components that allow the user to remotely control the operation of the modular dental tool 110 and/or the single-purpose dental tool 115. In the embodiment illustrated in FIG. 1, the one or more user input interfaces 207 includes a pressure-sensitive switch.

In one example, some or all of the components of the control module 155 may be included in or with the wireless foot pedal 120 or the docking station 105. Accordingly, the different functions performed by the components of the control module 155 may be also be performed by some or all of the components of the wireless foot pedal 120 and the docking station 105. In some embodiments, the different functions of the dental system 100 may be distributed individually or collectively between the control module 155, the wireless foot pedal 120, the docking station 105, or a combination thereof.

Figure 2:
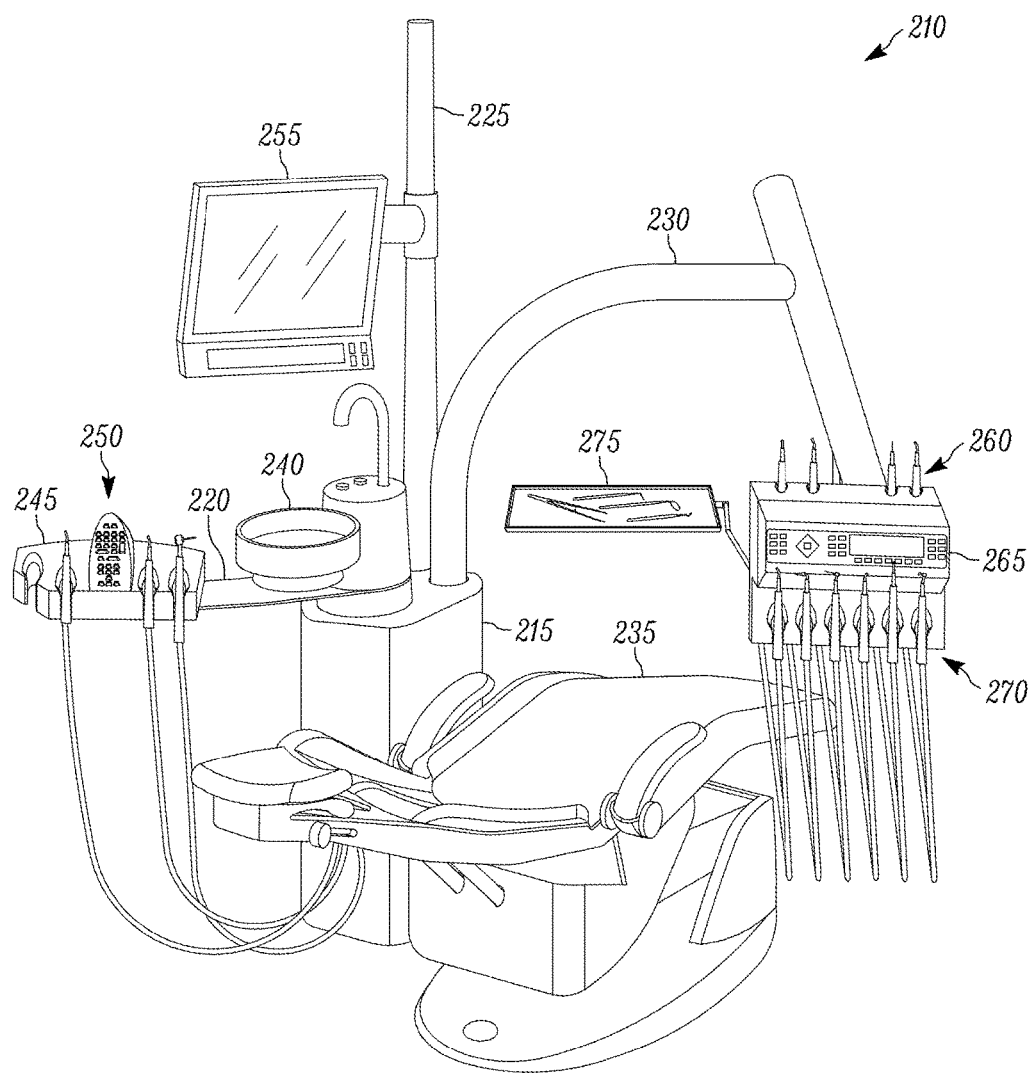
FIG. 2 is a diagram illustrating a treatment unit in accordance with some embodiments.

FIG. 2 is a diagram illustrating a treatment unit 210 in accordance with some embodiments. In the embodiment illustrated in FIG. 2, the treatment unit 210 includes a base 215, a first arm 220, a second arm 225, a third arm 230, a patient chair 235, a spit sink 240, a shelf 245, a first set of media-based dental tools 250, a display 255, a modular dental system 260, a dental tool control unit 265, a second set of media-based dental tools 270, and a dental tool tray 275.

In the example of FIG. 2, the base 215 is adjacent to the patient chair 235. The base 215 supports the first arm 220, the second arm 225, and the third arm 230. The first arm 220 supports the spit sink 240, the shelf 245, and the first set of media-based dental tools 250. The second arm 225 supports the display 255. The third arm 230 supports the modular dental system 260, the dental tool control unit 265, and the second set of media-based dental tools 270.

In the illustrated embodiment, the modular dental system 260 is integrated with the dental tool control unit 265 and supported by the third arm 230. In other embodiments, the modular dental system 260 is separate from the dental tool control unit 265. In yet other embodiments, the modular dental system 260 is supported by the first arm 220 or the second arm 225 instead of the third arm 230. For example, the modular dental system 260 may be integrated with the shelf 245 adjacent to the first set of media-based dental tools 250 and supported by the first arm 220.

In some embodiments, the modular dental system 260 is the same or similar to the dental system 100 described above. For example, the modular dental system 260 may include the docking station 105 and the display 255 may wirelessly or directly connect with the docking station 105 to function as the display 130 as described above. In some embodiments, the second arm 225 and the third arm 230 are hollow enclosures that include a set of wires that directly connect the modular dental system 260 to the display 255 via the treatment base 215.

Figure 3:
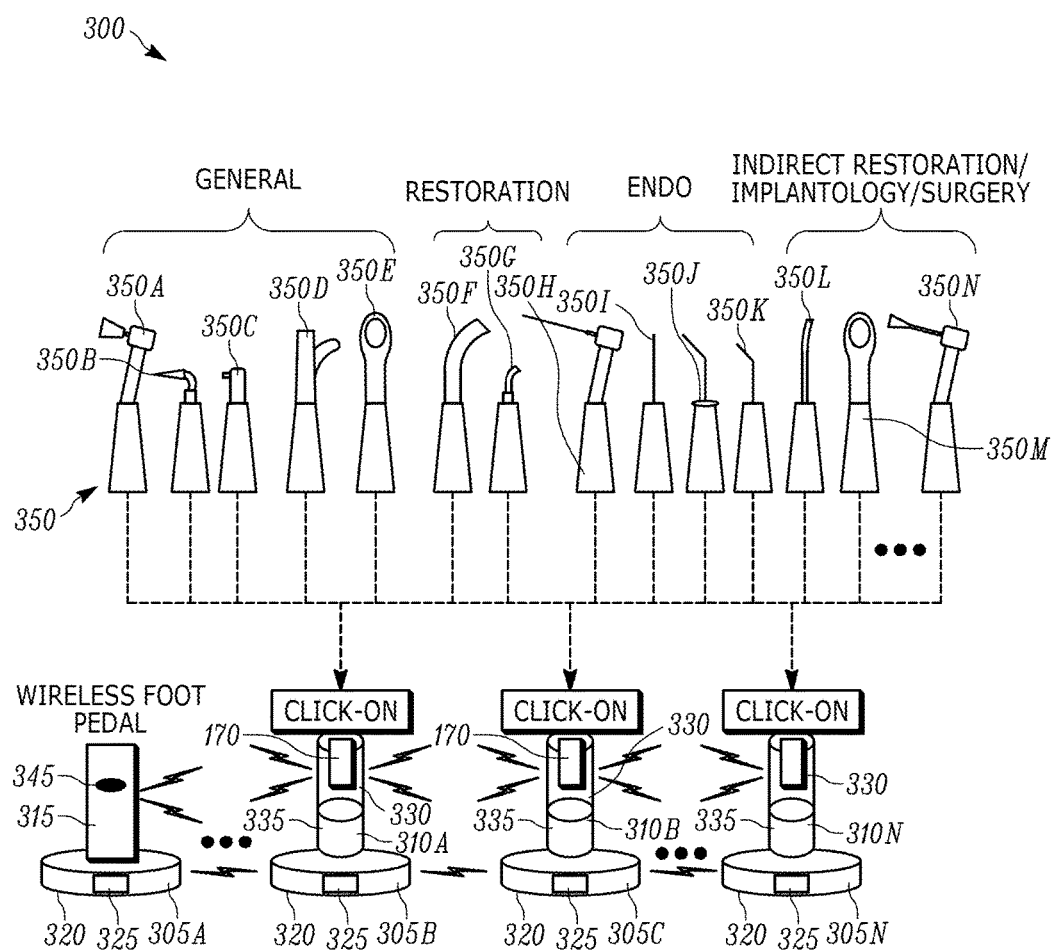
FIG. 3 is a diagram illustrating another dental system in accordance with some embodiments.

FIG. 3 is a diagram illustrating another dental system 300, in accordance with some embodiments. The dental system 300 includes individual docking stations 305A-305N (collectively referred to herein as "docking stations 305"), modular dental tools 310A-310N (collectively referred to herein as "modular dental tools 310"), and a wireless foot pedal 315. Each of the modular dental tools 310A-310N includes an control module 330, an interchangeable battery and any one of the several attachments 350A-350N (collectively referred to herein as "attachments 350") that may be used during a dental procedure.

The individual docking stations 305, the modular dental tools 310, and the wireless foot pedal 315 may be structurally and functionally similar to docking station 105, the modular dental tool 110, and the wireless foot pedal 120, respectively, and may also include similar components as described above.

For example, similar to the docking station 105, the docking stations 305 each include a housing 320 and a display 325. The docking stations 305 also include a control sub-system and a charging sub-system as described in greater detail below. The modular dental tools 310, similar to the modular dental tool 110, each include a control module 330 and a battery 335. The control module 330 may be similar or identical to the control module 155 as described in greater detail below. The battery 335 is also rechargeable. The wireless foot pedal 315, similar to the wireless foot pedal 120, includes a user input interface 345. As a consequence, the various similar aspects of these components are not described again in detail.

The attachment 150 as described above in FIG. 1 is represented by the attachment 350H in FIG. 3, also referred to as the endodontic drill attachment 350H.

Prior to performing a treatment or an operation, a user of the dental system 300 may select between different attachments 350 that may be attached to the control module 330, which in turn may be attached to battery 335 to form the modular dental tool 310. The attachments share common physical and communication features such that they are interchangeable in the sense that may be attached to and operate with the control module 330. The attachments are constructed so that an attachment may be removed from the control module and another attachment put in place (of the attachment that has been removed). In the embodiment illustrated in FIG. 3, to perform an endodontic treatment, the user selects the endodontic drill attachment 350H from the plurality of interchangeable attachments 350 and attaches the endodontic drill attachment 350H to the control module 330. Before or after attaching the endodontic drill attachment 350H, the user can view and adjust settings, parameters, or other variables of the various control sub-systems using the graphical user interface on the display of the docking station as described in greater detail below.

Additionally, in the embodiment illustrated in FIG. 3, each control sub-system of the docking stations 305, the modular dental tools 310, the wireless foot pedal 315, or some combination thereof, are configured to communicate with each other to perform various methods and techniques described herein. For example, each of the control modules 330 and/or the docking stations 305 may identify each of the attachments 350 with or without the attachments 350 being attached to the control modules 330 as will be described in greater detail below.

In some embodiments, some of the attachments 350 may include an electrical output device, which is referred to herein as a "driver." For example, the driver may be a linear motor, a rotary motor, or other suitable motor. In addition or alternatively, the driver may be or include an a light source, for example, a laser, lamp, or similar device. In some embodiments, the driver may be a removable module separate from the interchangeable attachments 350. In other embodiments, the driver is part of the control module 330 as will be described in greater detail below.

As illustrated by the dashed lines in FIG. 3, each of the attachments 350 may be attached to any of the control modules 330 to form a particular modular dental tool. For example, the modular dental tools 310 in conjunction with attachments 350 may be configured to function as one of a polisher, an ultrasonic driven device, a laser fluorescence, a trans-illumination device, an intraoral camera, a curing light, a powered composite extrusion device, a drill, an apex locator, a backfill, a downpack, a laser, a scanner, a screwdriver, or other non-media dependent dental tools.

The attachments 350 may be categorized into several groups including a general group, a restoration group, an endodontic group, and an indirect restoration/implantology/surgery group. The attachments 350A-350E are categorized as the "General" group and include the polisher attachment 350A, the ultrasonic driven attachment 350B, the laser fluorescence attachment 350C, the trans-illumination attachment 350D, and the intraoral camera attachment 350E. The interchangeable attachments 350F and 350G are categorized as the "Restoration" group and include the curing light attachment 350F and the powered composite extrusion attachment 350G. The attachments 350H-350K are categorized as the "Endo" group and include the endodontic drill attachment 350H, the apex locator attachment 350I, the backfill attachment 350J, and the downpack attachment 350K. The attachments 350L-350N are categorized as the "indirect restoration/implantology/surgery" group and include the laser attachment 350L, the intraoral scanner attachment 350M, and the screwdriver attachment 350N.

In the embodiment illustrated in FIG. 3, each of the modular dental tools 310 may be supported (for example, "docked") by one of the docking stations 305 to charge the battery 335 and store modular dental tools 310. In such an embodiment, each of the docking stations 305 includes an inductive electrical power source that may be used to transfer power to the battery 335 of modular dental tools 310.

Figure 4:
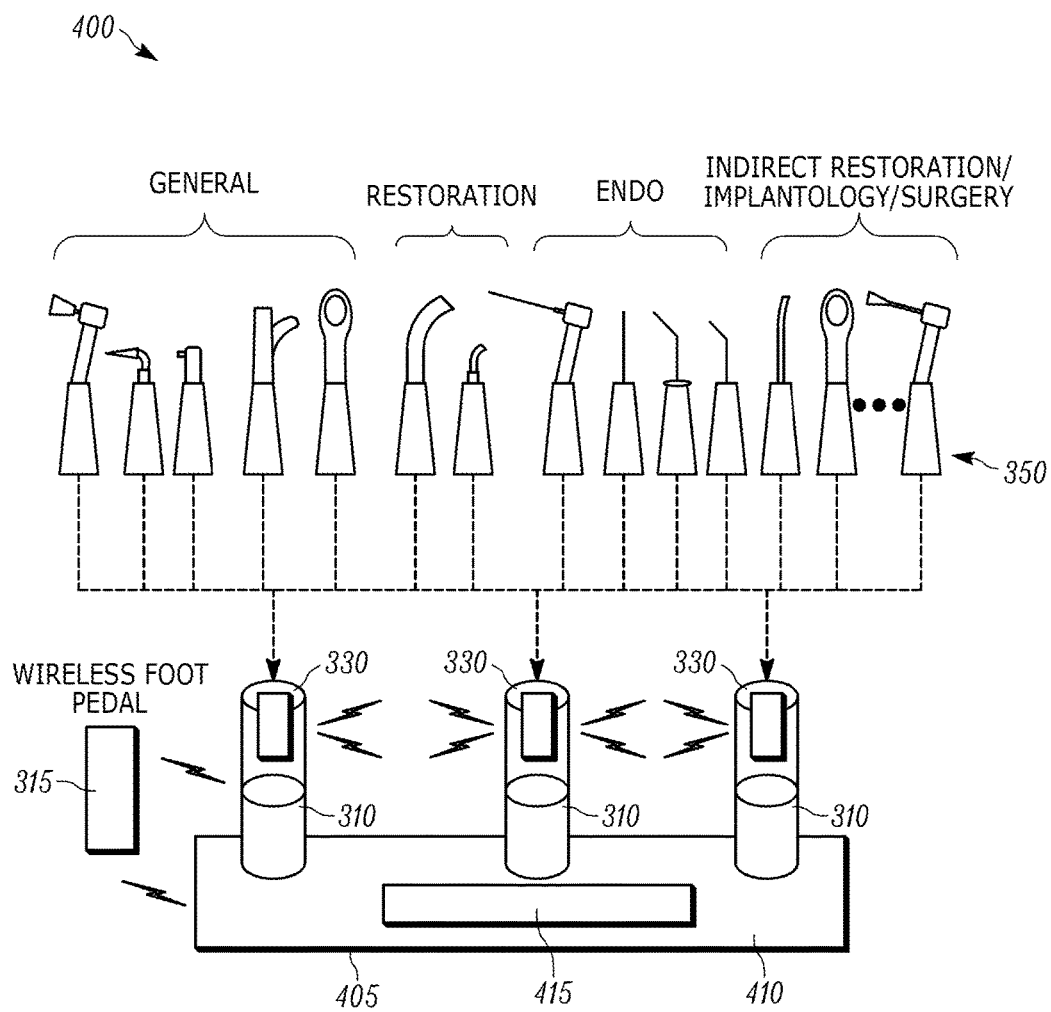
FIG. 4 is a diagram illustrating a dental system with a single docking station in accordance with some embodiments.

FIG. 4 is a diagram illustrating a dental system 400 with a single docking station 405, in accordance with some embodiments. As illustrated in FIG. 4, the single docking station 405 includes a housing 410 and a display 415 and is configured to communicate with all of the modular dental tools 310. In some embodiments, single docking station 405 also supports and communicates with a detachable wireless foot pedal 315. Each of the control modules 330 and/or the single docking station 405 is configured to identify each of the attachments 350 when it is either attached to or detached from the control modules 330 as will be described in greater detail below.

Figure 5:
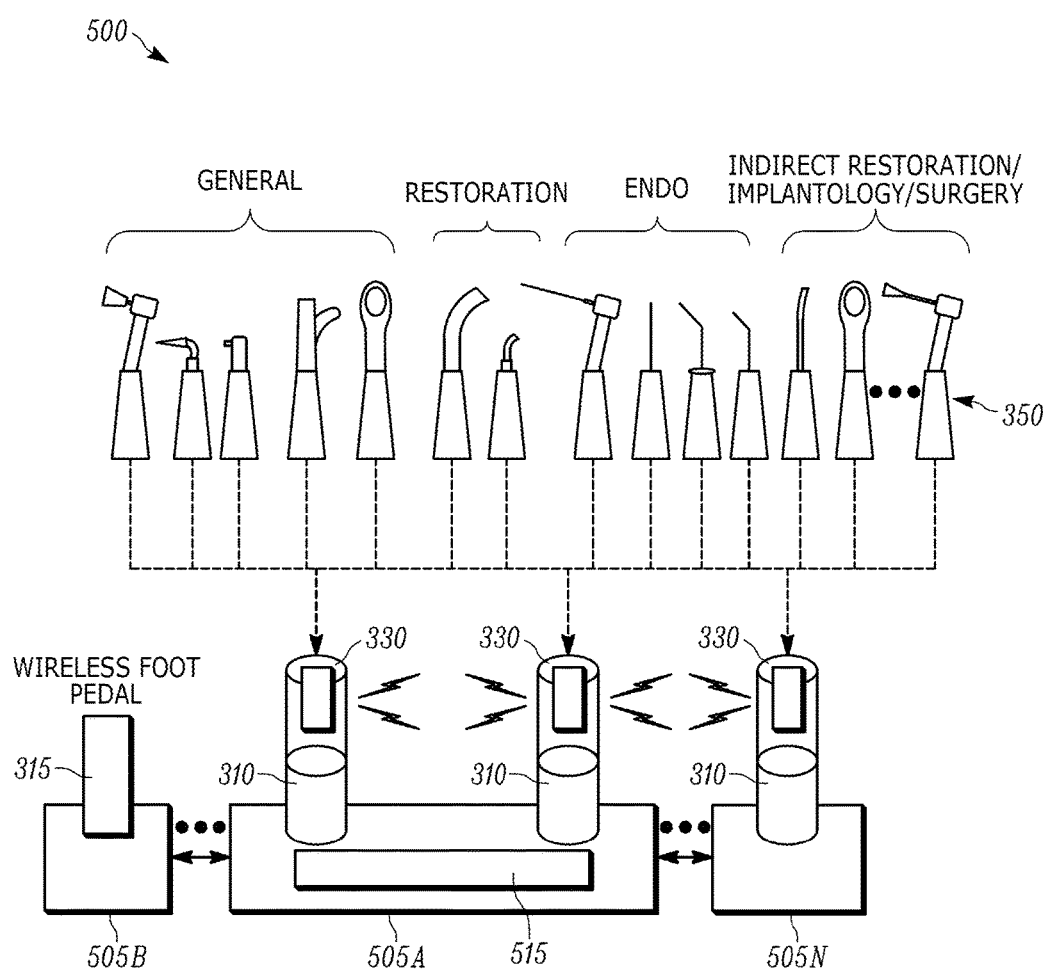
FIG. 5 is a diagram illustrating a dental system with individual docking station modules in accordance with some embodiments.

FIG. 5 is a diagram illustrating a dental system 500 with individual docking station modules 505A-505N (collectively referred to herein as "docking station 505"), in accordance with some embodiments. The docking station modules 505 are similar to the docking stations 305 and the single docking station 405 as described above. In some embodiments, docking station module 505A includes a display 515 that may be detachable.

The docking station modules 505 are configured to be attachable and removable from each other. In the embodiment illustrated in FIG. 5, the docking station modules 505B and 505N are attachable and removable from the docking station module 505A.

Additionally, in the embodiment illustrated in FIG. 5, each control sub-system of the docking station modules 505, the modular dental tools 310, the wireless foot pedal 315, or some combination thereof, are configured to communicate with each other to perform various methods and techniques described herein. For example, each of the control modules 330 and/or the docking station modules 505 may identify each of the attachments 350 with or without the attachments 350 being attached to the control modules 330 as will be described in greater detail below. In the example of FIG. 5, the docking station modules 505 may communicate with the modular dental tools 310 and the wireless foot pedal 315 through the physical docking of the modular dental tools 310 and the wireless foot pedal 315 or may communicate wirelessly. Additionally, the docking station modules 505 may communicate wirelessly with each other or communicate directly with each other when the docking station modules 505 are attached to each other.

Figure 6:
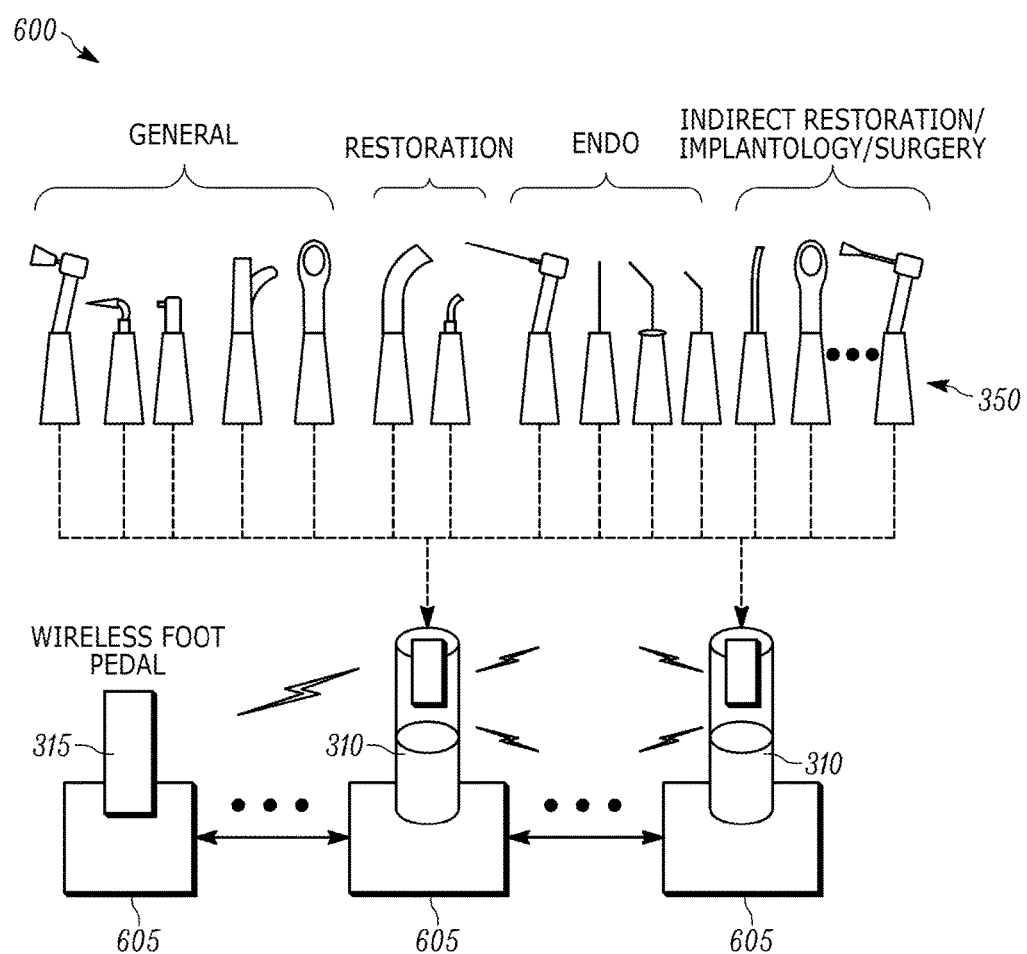
FIG. 6 is a diagram illustrating yet another dental system with individual docking stations in accordance with some embodiments.

FIG. 6 is a diagram that illustrates yet another dental system 600 with individual docking stations 605, in accordance with some embodiments. The docking stations 605 are similar to the docking station modules 505 described above.

In some embodiments, each of the docking stations 605 is configured to be attachable to and removable from each other. Additionally, each control sub-system of the docking stations 605 (shown in FIG. 6), the modular dental tools 310, the wireless foot pedal 315, or some combination thereof, are configured to communicate with each other to perform various methods and techniques described herein. For example, each of the control modules 330 and/or each of the docking stations 605 may identify each of the attachments 350 with or without the attachments 350 being attached to the control modules 330 as will be described in greater detail below. In the example of FIG. 6, the docking stations 605 may communicate with the modular dental tools 310 and the wireless foot pedal 315 through the physical docking of the modular dental tools 310 and the wireless foot pedal 315 or may communicate wirelessly. Additionally, the docking stations 605 may communicate wirelessly with each other or communicate directly with each other when the docking stations 605 are attached to each other.

Figure 7:
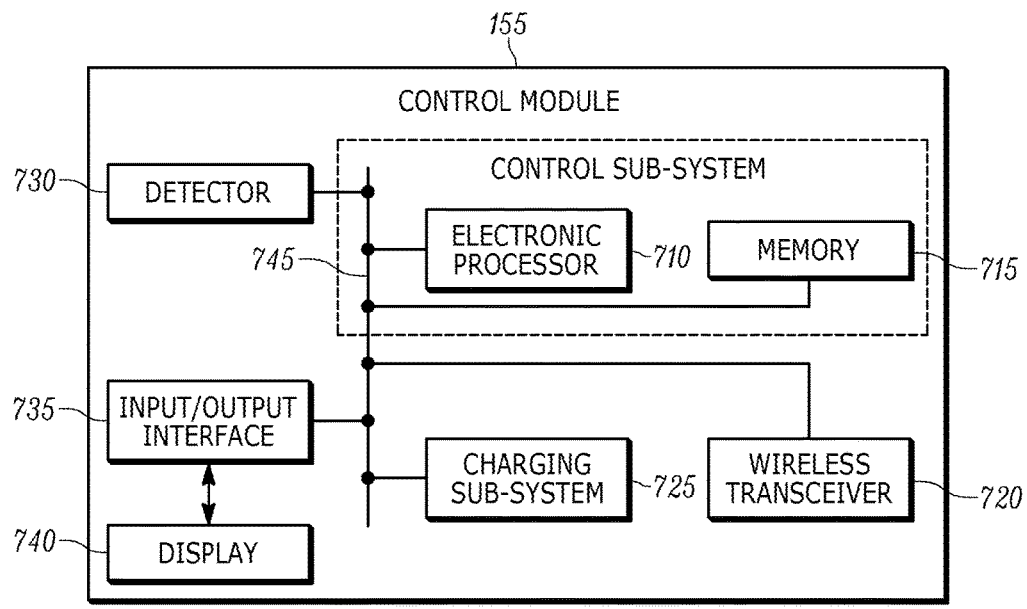
FIG. 7 is a block diagram illustrating the control module shown in FIG. 1, in accordance with some embodiments.

FIG. 7 is a block diagram illustrating the control module 155 shown in FIG. 1, in accordance with some embodiments. In the embodiment illustrated in FIG. 7, the control module 155 includes an electronic processor 710, a memory 715, a wireless transceiver 720, a charging sub-system 725, a detector 730, an input/output interface 735, a display 740, and a communication bus 745. In some embodiments, the control module 155 may include additional or different components than those components illustrated in FIG. 7 and may be configured to perform functionality other than or in addition to the functionality described herein.

In the embodiment illustrated in FIG. 7, the electronic processor 710, the memory 715, the wireless transceiver 720, the charging sub-system 725, the detector 730, and the input/output interface 735 are electrically and communicatively coupled to each other with the communication bus 745. However, the electronic processor 710, the memory 715, the wireless transceiver 720, the charging sub-system 725, the detector 730, and the input/output interface 735 may be electrically and communicatively coupled to each other in other ways without the communication bus 745.

The electronic processor 710 and the memory 715 form the control sub-system of the control module 155. For example, the software stored on the memory 715 may include instructions stored on a non-transitory computer-readable medium, that when executed, cause the electronic processor 710 to perform some or all of the methods described herein. In some embodiments, the electronic processor 710 is a microprocessor or an application-specific integrated circuit ("ASIC"), or other suitable processing device. In some embodiments, the memory 715 is a non-transitory computer-readable medium including random access memory ("RAM"), read-only memory ("ROM"), or other suitable non-transitory computer-readable medium.

The wireless transceiver 720 may include a one or more of a BLUETOOTH transceiver, a near-field communications (NFC) transceiver, a radio frequency (RF) transceiver, a Wi-Fi 802.11 transceiver, or other suitable wireless transceiver. The wireless transceiver 720 is capable of communicating with other wireless transceivers individually or collectively, or in some combination thereof over a wireless network. In some embodiments, the wireless network may include a Wi-Fi network, a BLUETOOTH network, a cellular network, or other suitable wireless network. For example, the electronic processor 710 may control the wireless transceiver 720 to perform pairing control and form a wireless BLUETOOTH network with other wireless transceivers.

The detector 730 wirelessly communicates with attached or unattached attachments (for example, the interchangeable attachments 350 as illustrated in FIGS. 2-5). In some embodiments, the detector 730 may include a radio frequency identification (RFID) device that communicates with radio frequency identification (RFID) tags. Each RFID tag contains a unique identifier that identifies the particular attachment from a plurality of interchangeable attachments. Instead of RFID tags, other mechanisms may be used to identify attachments or, in other words, detect an attachment identifier associated with the attachment when the attachment is removably attached to the first end of the control module 155. For example, in some embodiments, instead of the detector 730, the control module 155 may include a socket or similar component into which a plug or similar component is inserted and a connection (for example, resistance or other suitable electrical characteristic) or pin pattern may be used to determine the identity of an attachment from a plurality of attachments. For example, the electronic processor 710 may determine the pin pattern and compare the pin pattern to known pin patterns stored in the memory 715 to determine the identity of a particular attachment. Still other mechanisms for identifying the attachments may be used including, for example, graphical codes and code readers.

The input/output interface 735 communicates with systems and devices external to the control module 155. For example, the input/output interface 735 may communicate with the user input interface 175 as illustrated in FIG. 1 to receive inputs from the user. Additionally, the input/output interface 735 may output a graphical user interface to the display 740 (for example, the display 170 as illustrated in FIG. 1) and receive inputs from the user. The graphical user interface may be generated by the electronic processor 710 upon processing instructions stored in the memory 715. In an example, a set of graphical user interface elements may be generated and rendered to the display 740 when an attachment (for example, one of the interchangeable attachments 350 as illustrated in FIGS. 2-5) is attached to or removed from control module 155. In an example, the graphical user interface generated by the electronic processor 710 is different and unique to each of the various attachments (for example, the attachments 350) that are used in combination with control module 155.

Figure 8:
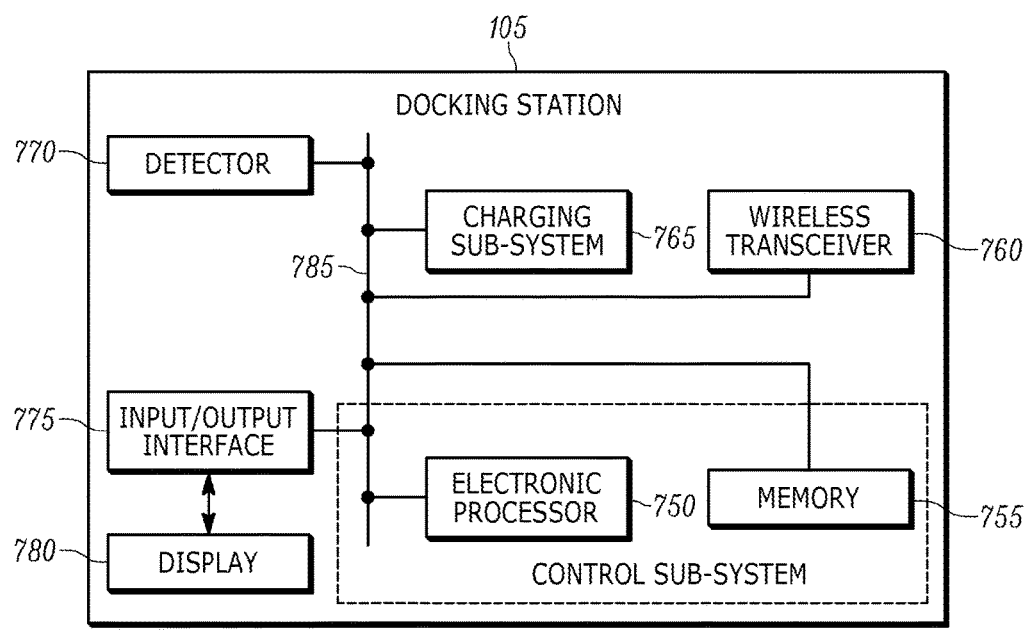
FIG. 8 is a block diagram illustrating the docking station shown in FIG. 1.

For example, FIG. 8 is a block diagram illustrating the docking station 105 shown in FIG. 1. In the example of FIG. 8, the docking station 105 includes an electronic processor 750, a memory 755, a transceiver 760, a charging sub-system 765, a detector 770, an input/output interface 775, a display 780, and a communication bus 785. In some embodiments, the docking station 105 may include additional or different components than those components illustrated in FIG. 8 and may be configured to perform additional functionality other than or in addition to the functionality described herein.

In the embodiment illustrated in FIG. 8, the electronic processor 750, the memory 755, the wireless transceiver 760, the charging sub-system 765, the detector 770, and the input/output interface 775 are electrically and communicatively coupled to each other with the communication bus 785. However, the electronic processor 750, the memory 755, the wireless transceiver 760, the charging sub-system 765, the detector 770, and the input/output interface 775 may be electrically and communicatively coupled to each other in other combinations without the communication bus 785.

The electronic processor 750 and the memory 755 form the control sub-system of the docking station 105. For example, the software stored on the memory 755 may include instructions stored on a non-transitory computer-readable medium, that when executed, cause the electronic processor 750 to perform some or all of the methods described herein. In some embodiments, the electronic processor 750 is a microprocessor or an application-specific integrated circuit ("ASIC"), or other suitable processing device. In some embodiments, the memory 755 is a non-transitory computer-readable medium including random access memory ("RAM"), read-only memory ("ROM"), or other suitable non-transitory computer-readable medium.

The wireless transceiver 760 may include a BLUETOOTH transceiver, a near-field communications (NFC) transceiver, a radio frequency (RF) transceiver, a Wi-Fi 802.11 transceiver, or other wireless suitable transceiver. The wireless transceiver 760 is capable of communicating with other wireless transceivers (for example, the wireless transceiver 720 as described above) individually or collectively, or in some combination thereof over a wireless network. In some embodiments, the wireless network may include a Wi-Fi network, a BLUETOOTH network, or other suitable wireless network. For example, the electronic processor 750 may control the wireless transceiver 760 to perform pairing control and form a wireless BLUETOOTH network with other wireless transceivers.

The detector 770 wirelessly communicates with attachments (for example, the attachments 350 as illustrated in FIGS. 2-5). In some embodiments, the detector 770 may include a radio frequency identification (RFID) device that communicates with radio frequency identification (RFID) tags. Each RFID tag contains a unique identifier that identifies the particular attachment a plurality of interchangeable attachments.

The input/output interface 775 communicates with systems and devices external to the docking station 105. For example, the input/output interface 775 may output a graphical user interface to the display 780 (for example, the display 130 as illustrated in FIG. 1) and receive inputs from the user. The graphical user interface may be generated by the electronic processor 750 upon processing instructions stored in the memory 755. For example, the graphical user interface may be uniquely generated for each different modular tool and/or single-purpose dental tool docked on the docking station 105.

The charging sub-system 765 includes a power source and inductive coils disposed in the three recesses 135, 140, and 145. The electronic processor 750 may control the charging sub-systems of the docking station 105, the modular dental tool 110, and the single-purpose dental tool 115 to charge the respective batteries of the modular dental tool 110 and the single-purpose dental tool 115. For example, the electronic processor 750 may control the charging sub-system to transfer power from a power source to the respective batteries via the respective inductive coils of the charging sub-system 765. In some embodiments, where the display 780 is a removable display, the electronic processor 750 may also control the charging sub-system 765 to charge a rechargeable battery of the display 780. For example, the electronic processor 750 may control the charging sub-system 765 to transfer power from the power source to the battery of the display 780 via an inductive coil, a power cable, or other suitable power connection.

Figure 9:
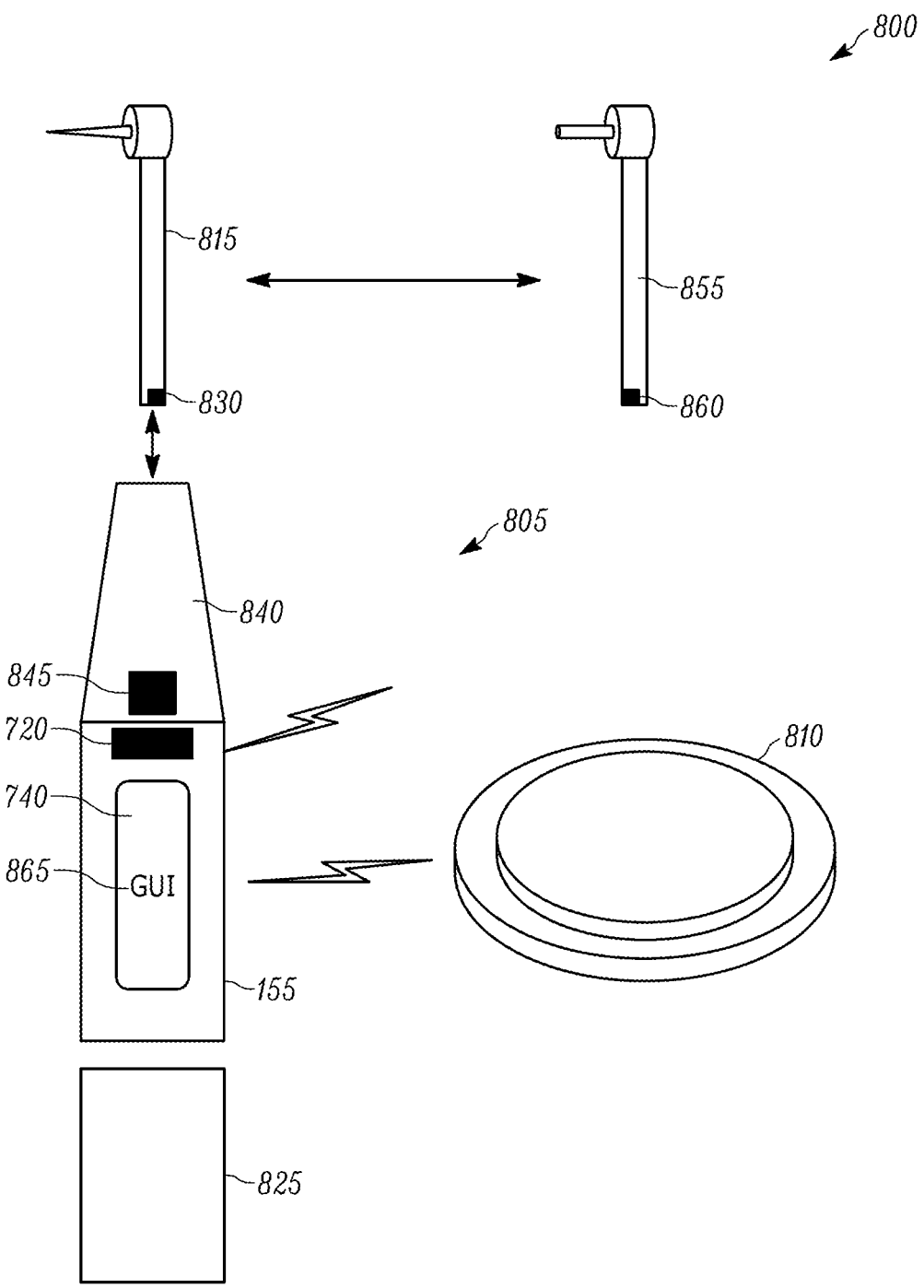
FIGS. 9-12 are diagrams illustrating other dental systems, in accordance with various embodiments.

FIGS. 9-12 are diagrams illustrating other dental systems, in accordance with various embodiments. For example, FIG. 9 is a diagram illustrating an exemplary dental system 800. The dental system 800 includes a modular dental tool 805 and a wireless foot pedal 810 that include components similar to components of the modular dental tool 110 and the wireless foot pedal 120, respectively, as described above.

In some embodiments, the modular dental tool 805 includes an interchangeable attachment 815, a control module 155 (shown in FIG. 7), and interchangeable battery 825 (described herein as "battery 825"). The battery 825 is rechargeable. The interchangeable attachment 815 includes a transmitter 830 that is configured to transmit a unique identifier associated with interchangeable attachment 815. In some embodiments, the control module 155 includes a driver 840, a detector 845 a wireless transceiver 720, and a display 740. In the embodiment illustrated in FIG. 9, the interchangeable attachment 815 is an endodontic drill. In some embodiments, the attachment 815 may be swapped with a second attachment 855. In some embodiments, the second attachment 855 includes a transmitter 860 configured to transmit a unique identifier associated with the attachment 855.

In some embodiments, the detector 845 is configured to receive information from the transmitter 830 when the interchangeable attachment 815 is removably attached to the control module 155. In some embodiments, the detector 845 includes a radio frequency identification (RFID) device that wirelessly communicates with or interrogates a radio frequency identification (RFID) tags that transmit unique identifiers associated with interchangeable attachments, including, for example, the interchangeable attachments 815 and 855. The detector 845 is configured to provide the identification information received from the interchangeable attachments 815 and 855 to an electronic processor (similar to the electronic processor 710 shown in FIG. 8), which can look up the type of the interchangeable attachment from a lookup table stored in a memory (similar to the memory 715 shown in FIG. 8).

In some embodiments, the electronic processor is configured to use the identification information received from either of interchangeable attachments 815 and 855 to process instructions stored in the memory and generate a graphical user interface 865 that allows a user to control and operate the attachments 815 and 855. In other embodiments, the electronic processor may also control the display 740 to remove the graphical user interface 865 when there is no particular graphical user interface associated with the unique identifier. The deactivation of the graphical user interface 865 may prevent unintentional inputs from being received with the graphical user interface 865. The electronic processor may also perform similar operations with the transmitter 860 and other transmitters.

Additionally, the electronic processor may use the identification information from the transmitter 830 to determine whether the driver 840 is compatible with attachment 815. Similarly, the electronic processor may use the identification information from the transmitter 860 to determine whether the driver 840 is compatible with the unattached attachment 855.

When the electronic processor determines that the driver 840 is not compatible with the attachments 815 or 855, the electronic processor may control the graphical user interface 865 to output an alert to the user that the driver 840 is not compatible with the particular attachment. When the electronic processor determines that the driver 840 is compatible with the attachments 815 or 855, the electronic processor may control the graphical user interface 865 to output an alert to the user that the driver 840 is compatible with the particular attachment.

In other embodiments, the electronic processor may control a transducer to output audible alerts to the user indicating whether the driver 840 is compatible with the particular attachment. For example, one tone when the driver is compatible and a second, different tone when the driver is not compatible. In yet other embodiments, the electronic processor may control a tactile device to output a tactile alert to the user indicating whether the driver 840 is compatible with the particular attachment.

Figure 10:
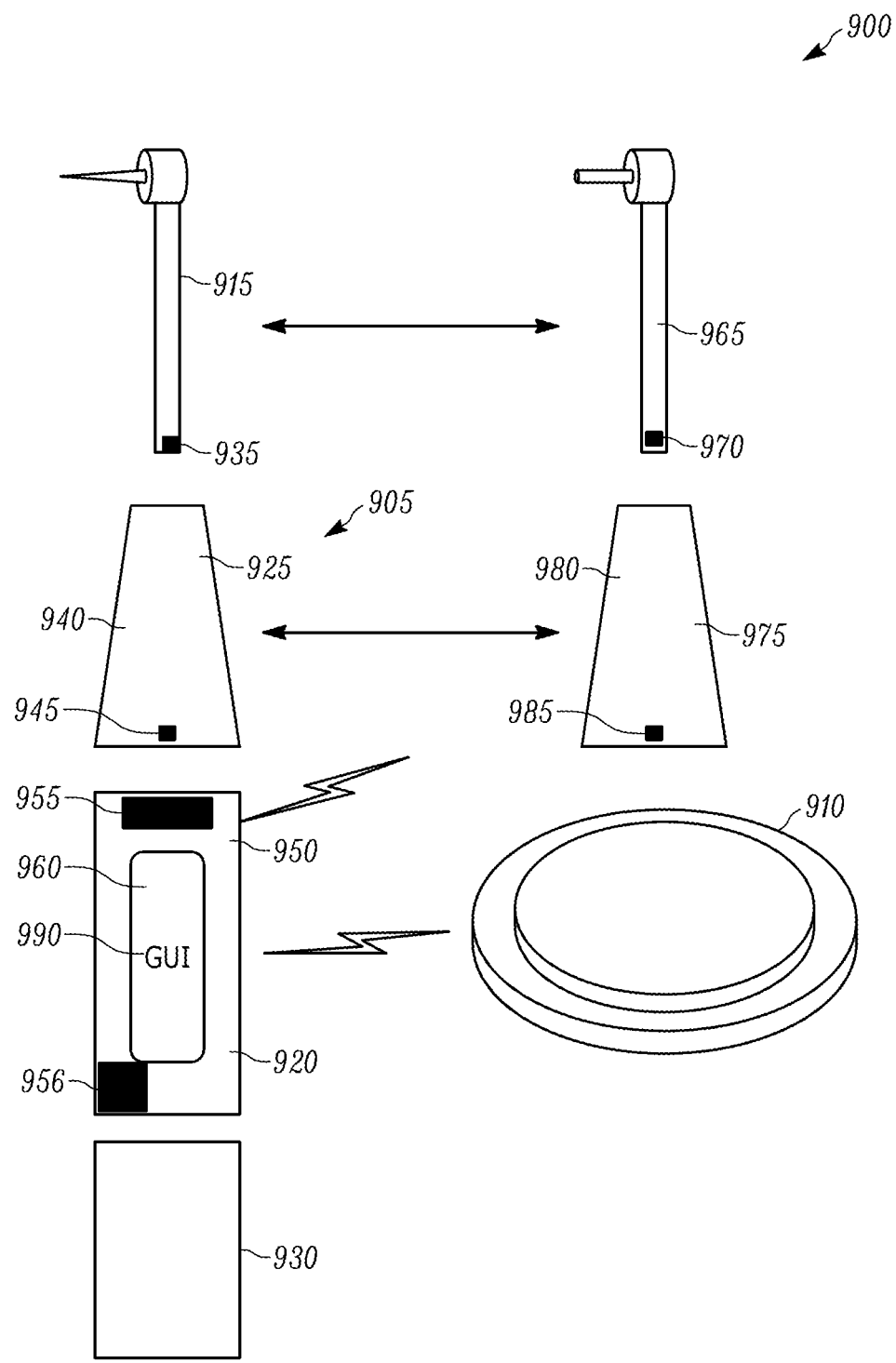

FIG. 10 is a diagram illustrating another dental system 900. In the example of FIG. 10, the dental system 900 includes a modular dental tool 905 and a wireless foot pedal 910 that includes components similar to components of the modular dental tool 805 and the wireless foot pedal 810, respectively, as described above.

In some embodiments, the modular dental tool 905 includes an attachment 915, a control module 920, a driver module 925, and a battery 930 (described herein as "battery 930"). The battery 930 is also rechargeable. The attachment 915 includes a first transmitter 935 configured to transmit a first unique identifier. The driver module 925 includes a housing 940 and a transmitter 945 configured to provide a second unique identifier that is unique to the first unique identifier. In some embodiments, the first unique identifier is associated with one more characteristics of attachment 915 (for example, a part number, a part type, or other characteristic). The control module 920 includes a housing 950, a transceiver 955, a detector 956, and a display 960. In the embodiment of FIG. 10, the attachment 915 is an endodontic drill. However, the attachment 915 may be swapped with a second interchangeable attachment 965. The second attachment 965 has a transmitter 970 that is configured to provide a third unique identifier that is unique to all other unique identifiers including unique the first and second unique identifiers. Similarly, the driver module 925 may be swapped with a second driver module 975. The second driver module 975 includes a housing 980 and a transmitter 985 that is configured to transmit a fourth unique identifier that is unique to all other unique identifiers including unique the first, second, and third unique identifiers.

In example provided, the control module 920 includes a control sub-system and a charging sub-system that is similar to the control sub-system and the charging sub-system as described in detail above. In some embodiments, an electronic processor in control module 920 is configured to generate a graphical user interface 990 and display the graphical user interface 990 on the display 960 based on processing of instructions stored in a memory within the control module 920.

In some embodiments, the detector 956 may wirelessly communicate with the transmitter 935, the transmitter 945, the transmitter 970, the transmitter 985, or a combination thereof. For example, the detector 956 is a radio frequency identification (RFID) device that communicates with or interrogates the radio frequency identification (RFID) tag associated with each of the transmitter 935, the transmitter 945, the transmitter 970, and the transmitter 985 (collectively "transmitters"). The detector 956 may determine a unique identifier from each of the transmitters. In some embodiments, the detector 956 provides the unique identifier to an electronic processor, which can look up the identification information (for example, the type) of the interchangeable attachment or interchangeable driver from a lookup table stored in a memory.

When an electronic processor within control module 920 determines that the driver module 925 is not compatible with the attachments 915 or 965, the electronic processor may generate a graphical user interface 990 to display on the display 960 notifying the user that attachments 915 or 965 is not compatible with the driver module 925. When the electronic processor determines that the driver module 925 is compatible with the interchangeable attachments 915 or 965, the electronic processor may generate a graphical user interface 990 to display on the display 960 that the attachments 915 or 965 are compatible for the particular attachment.

In other embodiments, the electronic processor may control a transducer to output an audible alert to inform the user whether the interchangeable driver module 925 is compatible with the particular interchangeable attachment. In yet other embodiments, the electronic processor may control a tactile device to output a tactile alert to the user that the interchangeable driver module 925 is compatible with the particular interchangeable attachment.

Figure 11:
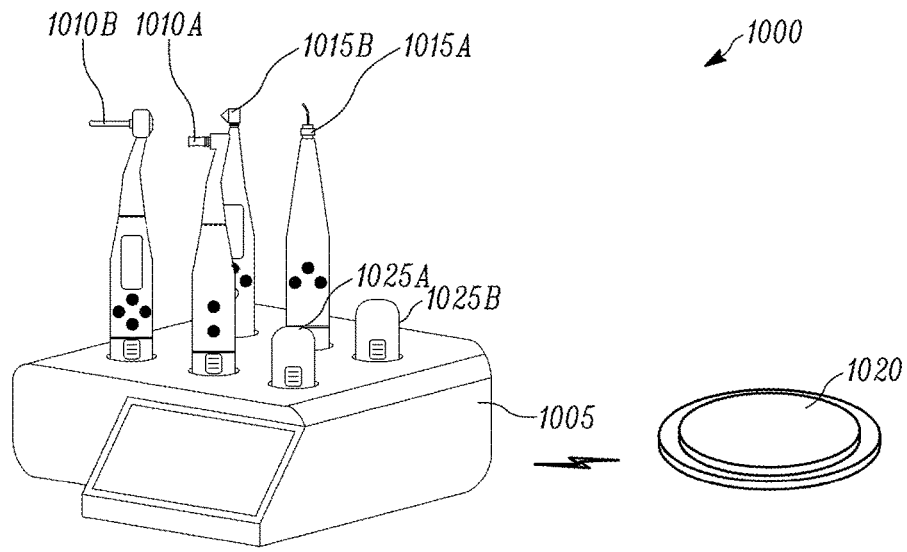

FIG. 11 is a diagram illustrating another dental system 1000. In the example of FIG. 11, the dental system 1000 includes a docking station 1005, two modular dental tools 1010A and 1010B (collectively referred to herein as "modular dental tools 1010"), two single-purpose dental tools 1015A and 1015B (collectively referred to herein as "single-purpose dental tools 1015"), a wireless foot pedal 1020, and two rechargeable batteries 1025A and 1025B (collectively referred to herein as "rechargeable batteries 1025"). The docking station 1005 has components that are similar to the components of the docking stations described above. The modular dental tools 1010 have components that are similar to the components of the modular dental tools described above. The single-purpose dental tools 1015 have components that are similar to the components of the single-purpose dental tools described above. The wireless foot pedal 1020 includes components that are similar to the components of the wireless foot pedal described above. The docking station 1005 is capable of simultaneously charging the modular dental tools 1010, the single-purpose dental tools 1015, and the rechargeable batteries 1025.

In some embodiments, docking station 1005 includes an electronic processor configured to generate several graphical user interfaces to be displayed, which allows a user to view various aspects and/or features of the modular dental tools 1010 and the single-purpose dental tools 1015. In one example, the graphical user interface may display, on the display provided in the docking station 1005, the amount of use time remaining for that the modular dental tools 1010 and single-purpose dental tools 1015. In another example, the graphical user interface may display the amount of charge the rechargeable battery 1025 is carrying. In another example, the graphical user interface may display, a listing of a number of available attachments that are nearby and tracked by the docking station. In yet another example, the graphical user interface may display additional or expanded control features for improved functionality of the modular dental tools 1010 and/or the single-purpose dental tools 1015, including, for example, a "health" of the tools (for example, whether one or more components of the tool have failed); and a maintenance state (for example, whether maintenance of various components is required). In addition, the graphical user interface may display information regarding the modular and single-purpose tools that have been associated with the dental system and are, for example, available for use.

Figure 12:
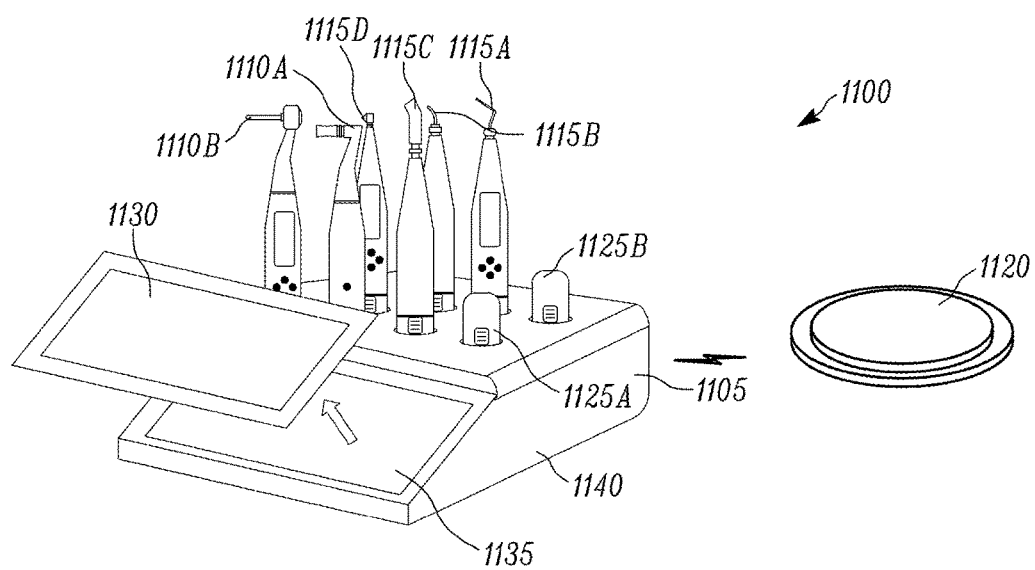

FIG. 12 is a diagram illustrating another dental system 1100. In the example of FIG. 12, the dental system 1100 includes a docking station 1105, two modular dental tools 1110A and 1110B (collectively "modular dental tools 1110"), four single-purpose dental tools 1115A-1115D (collectively "single-purpose dental tools 1115"), a wireless foot pedal 1120, and two interchangeable and rechargeable batteries 1125A and 1125B (collectively "interchangeable and rechargeable batteries 1125"). In an example, docking station 1105 includes a display 1130 that is detachable or removable. The display 1130 is configured to display one or more graphical user interfaces that are generated by an electronic processor in the docking station 1105 that processes a set of instructions stored in a memory within the docking station. The docking station 1105 has components that are similar to the components of the docking stations described above. The modular dental tools 1110 have components that are similar to the components of the modular dental tools described above. The single-purpose dental tools 1115 have components that are similar to the components of the single-purpose dental tools described above. The wireless foot pedal 1120 includes components similar to the components of the wireless foot pedal described above. As a consequence these similar components are not described again in detail. In the embodiment illustrated in FIG. 12, the display 1130 of the docking station 1105 is removable from a recess 1135 in a housing 1140 of the docking station 1105. In some embodiments, the display 1130 is removable from a structure without a recess.

Figure 13:
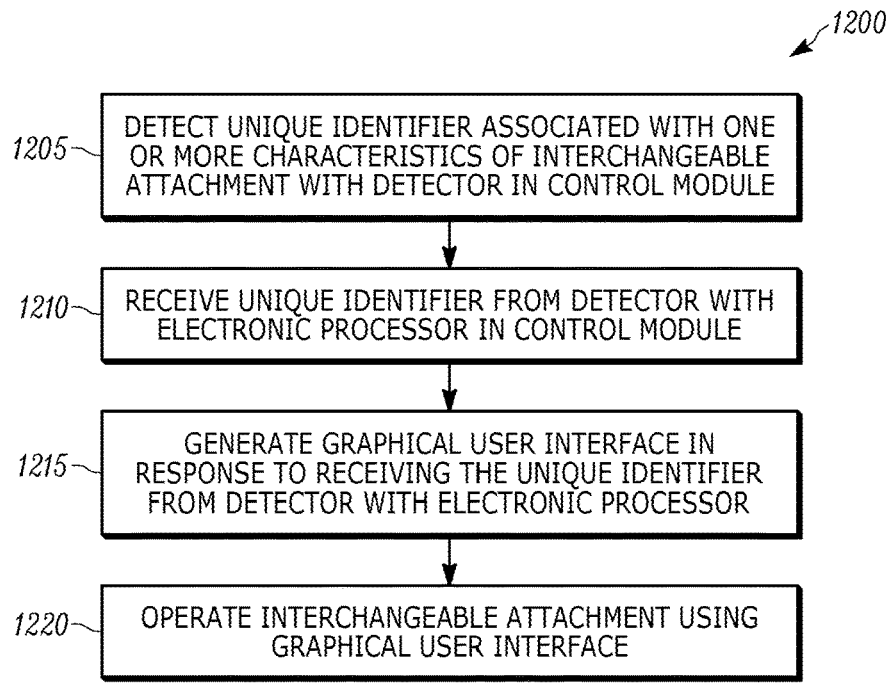
FIG. 13 is a flowchart showing a method for controlling a modular dental tool in accordance with some embodiments.

FIG. 13 is a flowchart showing a method 1200 for controlling a modular dental tool in accordance with some embodiments. FIG. 13 is described from the perspective of the control module 155 of FIG. 7. However, FIG. 13 is also applicable from the perspective of the modular dental tools 805 and 905 of FIGS. 8 and 9.

The electronic processor 710 controls the detector 730 to detect a unique identifier associated with one or more characteristics of an interchangeable attachment (for example, the attachment 150 of FIG. 1) (at block 1205). For example, the electronic processor 710 controls a radio frequency identification reader to detect a radio frequency identification (RFID) tag having a unique identifier and attached to the endodontic drill attachment 150.

The electronic processor 710 receives the unique identifier from the detector 730 (at block 1210). For example, the electronic processor 710 receives the unique identifier over the communication bus 745.

In response to receiving the unique identifier, the electronic processor 710 generates a graphical user interface based on the unique identifier (at block 1215). For example, the electronic processor 710 generates a graphical user interface with controls associated with the endodontic drill attachment 150 as will be described in greater detail below.

The electronic processor 710 operates the interchangeable attachment using the graphical user interface (at block 1220). For example, the electronic processor 710 controls a driver to drive the endodontic drill attachment 150 in response to receiving an input associated with the graphical user interface displayed on the display 740.

In some embodiments, the electronic processor 710 controls the display 740 to output a graphical user interface on the display 740. For example, the electronic processor 710 controls the display 740 to output the graphical user interface with controls associated with the endodontic drill attachment 150.

In other embodiments, the electronic processor 710 transmits the graphical user interface to the docking station 105 via the wireless transceivers 720 and 760 interface over a wireless network. In these embodiments, the electronic processor 710 may also control the display 780 of the docking station 105 to output the graphical user interface via the wireless transceivers 720 and 760 communicating over the wireless network.

Figure 14:
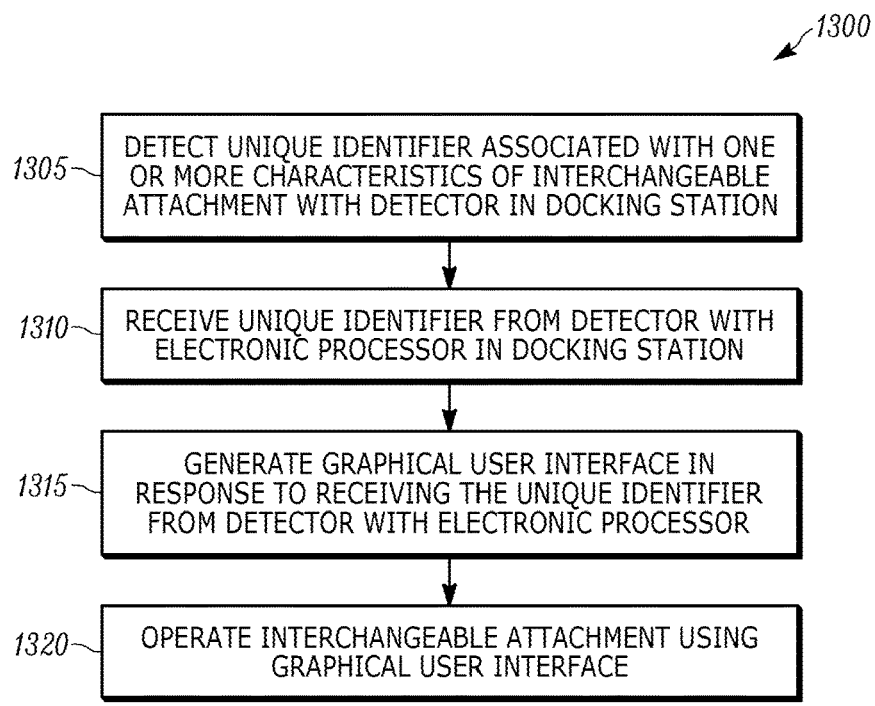
FIG. 14 is a flowchart showing another method for controlling a modular dental tool in accordance with some embodiments.

FIG. 14 is a flowchart showing another method 1300 for controlling a modular dental tool in accordance with some embodiments. The method 1300 is described from the perspective of the docking station 105 of FIG. 8.

The electronic processor 750 controls the detector 770 to detect a unique identifier associated with one or more characteristics of an interchangeable attachment (for example, the attachment 150 of FIG. 1) (at block 1305). For example, the electronic processor 750 controls a radio frequency identification reader to detect a radio frequency identification (RFID) tag having a unique identifier and attached to the endodontic drill attachment 150.

The electronic processor 750 receives the unique identifier from the detector 770 (at block 1310). For example, the electronic processor 750 receives the unique identifier over the communication bus 785.

In response to detecting the attachment, the electronic processor 750 generates a graphical user interface based on the unique identifier (at block 1315). For example, the electronic processor 750 generates the graphical user interface with controls associated with the endodontic drill attachment 150.

The electronic processor 750 operates the interchangeable attachment using the graphical user interface (at block 1320). For example, the electronic processor 750 controls a driver to drive the endodontic drill attachment 150 in response to receiving an input associated with the graphical user interface.

In some embodiments, the electronic processor 750 controls the display 780 to output the graphical user interface. For example, the electronic processor 750 controls the display 780 to output the graphical user interface with controls associated with the endodontic drill attachment 150.

In other embodiments, the electronic processor 750 transmits the graphical user interface to the control module 155 via the wireless transceivers 760 and 720 communicating over a wireless network. In these embodiments, the electronic processor 750 may also control the display 740 of the control module 155 to output the graphical user interface via the wireless transceivers 760 and 720 communicating over a wireless network.

FIG. 15 is a diagram showing a graphical user interface 1400 for controlling an endodontic drill attachment 350H in accordance with some embodiments. The graphical user interface 1400 includes a rotations-per-minute selector 1402, a torque selector 1404, an apex length output 1406, and a battery indicator 1408.

FIG. 16 is a diagram showing a graphical user interface 1500 for controlling a backfill attachment 350J in accordance with some embodiments. The graphical user interface 1500 includes a gutta percha selection button 1502, synthetic composite selection button 1504, custom button 1506, a temperature selector 1508, and a battery indicator 1510.

FIG. 17 is a diagram showing a graphical user interface 1600 for controlling an ultraviolet (UV) curing light attachment 350F in accordance with some embodiments. The graphical user interface 1600 includes a five second timer button 1602, a ten second timer button 1604, a twenty second timer button 1606, and a battery indicator 1608.

It should be understood that FIGS. 15 through 17 illustrate examples and that the graphical user interfaces could include additional or alternative features and elements.

Various features and embodiments are set forth in the following claims.

What is claimed is:

1. A modular dental system comprising:
a control module including
a first end,
a second end,
a control sub-system configured to
communicatively couple to an attachment,
detect an attachment identifier associated with the attachment when the attachment is removably attached to the first end of the control module, and
control the attachment based on the attachment identifier, and
a charging sub-system;
a battery module configured to removably attach to the second end of the control module; and
a driver module configured to removably attach to the first end of the control module and removably attach to a second attachment that is different from the attachment.

2. The modular dental system of claim 1, further comprising a docking station.

3. The modular dental system of claim 2, wherein the docking station is configured to communicatively couple to the control module, the battery module, and the attachment.

4. The modular dental system of claim 2, wherein the docking station is configured to couple to a treatment unit.

5. The modular dental system of claim 2, further comprising:
a modular dental tool including the control module, the battery module, and the driver module,
wherein the docking station includes:
a display; and
a housing configured to support the modular dental tool and the display, and
wherein the docking station is communicably coupled to the control sub-system when the modular dental tool is removably attached to the docking station.

6. The modular dental system of claim 5, wherein the housing is further configured to support a single-purpose dental tool.

7. The modular dental system of claim 6, wherein the docking station includes a graphical user interface that is configured to control at least one of the control module and the attachment.

8. The modular dental system of claim 7, further comprising an input control, wherein the housing is further configured to support and dock the single-purpose dental tool having a second battery.

9. The modular dental system of claim 8, wherein the input control is a wireless foot pedal having a third battery.

10. The modular dental system of claim 7, wherein the docking station is configured to detect the attachment identifier.

11. The modular dental system of claim 1, further comprising a plurality of docking stations, each of the plurality of docking stations including
a housing configured to support at least one battery module and a wireless foot pedal; and
a docking station charging sub-system configured to charge at least one of the at least one battery module and the wireless foot pedal.

12. The modular dental system of claim 11, wherein each of the plurality of docking stations is configured to removably attach to each other to form a single docking station.

13. The modular dental system of claim 12, wherein each of the plurality of docking stations is configured to be electrically and communicatively coupled to each other when the plurality of docking stations form the single docking station.

14. The modular dental system of claim 12, wherein at least one of the plurality of docking stations further includes a second display configured to communicatively couple to a second control module.

15. The modular dental system of claim 1, further comprising a wireless foot pedal including a user input interface, the wireless foot pedal configured to communicate one or more user inputs from the user input interface to the control sub-system.

16. The modular dental system of claim 1, wherein the control module further includes a display and a first user input interface.

17. The modular dental system of claim 1, wherein the driver module further includes a driver configured to drive the attachment.

18. The modular dental system of claim 17, wherein the driver comprises one selected from a group consisting of linear motor and a rotary motor.

19. A dental system comprising:
a first modular dental tool including
a first control module including
a first control sub-system, and
a first charging sub-system;
a first battery module configured to removably attach to the first charging sub-system at a first end of the first control module;
a first attachment configured to removably attach to a second end of the first control module opposite from the first end;
a second attachment configured to removably attach to the second end of the first control module in place of the first attachment;
a second battery module configured to removably attach to the first charging sub-system at the first end of the first control module in place of the first battery module; and
a second control module configured to removably attach to the first battery module and the first attachment, wherein the first attachment and the second attachment are different types of dental attachments; and
a driver module configured to removably attach to the first end of the control module and removably attach to a third attachment that is different from the first attachment and the second attachment.

20. The dental system of claim 19, further comprising a second modular dental tool that includes the second control module and the second control module includes
a second control sub-system, and
a second charging sub-system;
the second battery module configured to removably attach to the second charging sub-system at a first end of the second control module; and
the second attachment configured to removably attach to a second end of the second control module.

21. A treatment unit comprising:
a modular dental system having
a control module including
a first end,
a second end,
a control sub-system configured to
communicatively couple to an attachment,
detect an attachment identifier associated with the attachment when the attachment is removably attached to the first end of the control module, and
control the attachment based on the attachment identifier;
a charging sub-system; and
a battery module configured to removably attach to the second end of the control module;
a driver module configured to removably attach to the first end of the control module and removably attach to a second attachment that is different from the attachment; and
a docking station.

22. A modular dental system comprising:
a control module including
a first end,
a second end,
a control sub-system configured to
communicatively couple to an attachment,
detect an attachment identifier associated with the attachment when the attachment is removably attached to the first end of the control module, and
control the attachment based on the attachment identifier, and
a charging sub-system;
a battery module configured to removably attach to the second end of the control module,
wherein the control sub-system is further configured to wirelessly detect a second attachment identifier associated with a second attachment when the attachment is removably attached to the first end of the control module, the second attachment being detached from the first end of the control module.

23. The modular dental system of claim 1, wherein the charging sub-system is configured to control a charging of the battery module.

24. A modular dental system comprising:
a control module including
a first end,
a second end,
a control sub-system including an electronic processor and a memory, the electronic processor is electrically connected to the memory, and the electronic processor is configured to
communicatively couple to an attachment,
detect an attachment identifier associated with the attachment when the attachment is removably attached to the first end of the control module, and control the attachment based on the attachment identifier, and
a charging sub-system;
a battery module configured to removably attach to the second end of the control module; and
a driver module configured to removably attach to the first end of the control module and removably attach to a second attachment that is different from the attachment.

* * * * *